(12) United States Patent
Solazzi

(10) Patent No.: US 7,722,821 B2
(45) Date of Patent: May 25, 2010

(54) SAMPLE CUP FOR USE IN X-RAY SPECTROSCOPY WITH INTERNAL OVERFLOW RESERVOIR

(75) Inventor: Monte J. Solazzi, Palm City, FL (US)

(73) Assignee: Chemplax Industries, Inc., Palm City, FL (US)

( * ) Notice: Subject to any disclaimer, the term of this patent is extended or adjusted under 35 U.S.C. 154(b) by 639 days.

(21) Appl. No.: 10/990,994

(22) Filed: Nov. 17, 2004

(65) Prior Publication Data

US 2006/0104867 A1    May 18, 2006

(51) Int. Cl.
*B01L 3/00* (2006.01)

(52) U.S. Cl. ............ 422/102; 378/208; 73/864.91

(58) Field of Classification Search .......... 422/102; 378/208; 73/864.91
See application file for complete search history.

(56) References Cited

U.S. PATENT DOCUMENTS

| | | | |
|---|---|---|---|
| D238,693 S | 2/1976 | Solazzi | |
| 4,409,854 A | 10/1983 | Solazzi | |
| 4,448,311 A | 5/1984 | Houser | |
| 4,575,869 A * | 3/1986 | Torrisi et al. | ........... 378/47 |
| 4,643,033 A | 2/1987 | Solazzi | |
| 4,665,759 A | 5/1987 | Solazzi | |
| 4,698,210 A * | 10/1987 | Solazzi | ........... 422/102 |
| 4,974,244 A | 11/1990 | Torrisi | |
| 4,986,965 A * | 1/1991 | Ushikubo | ........... 422/102 |
| 5,253,280 A | 10/1993 | Mizuta | |
| 5,323,441 A | 6/1994 | Torrisi | |
| 5,451,375 A | 9/1995 | Solazzi | |
| 5,454,020 A | 9/1995 | Solazzi | |
| 5,630,989 A | 5/1997 | Solazzi | |
| 6,603,544 B1 | 8/2003 | Eckert | |

* cited by examiner

*Primary Examiner*—Lyle A Alexander
*Assistant Examiner*—Dennis M White
(74) *Attorney, Agent, or Firm*—Plevy & Keens, LLP

(57) ABSTRACT

A sample cup for retaining a sample material to be subjected to an x-ray spectrochemical analysis. The sample cup comprises a cell body of a cylindrical configuration having an open top end and an open bottom end and defining a hollow between the two open ends, the open top end having an outer wall and an inner wall encircling the open top end. The outer wall and the inner wall extend axially and are positioned in concentric relationship with one another and form a reservoir space therebetween.

16 Claims, 5 Drawing Sheets

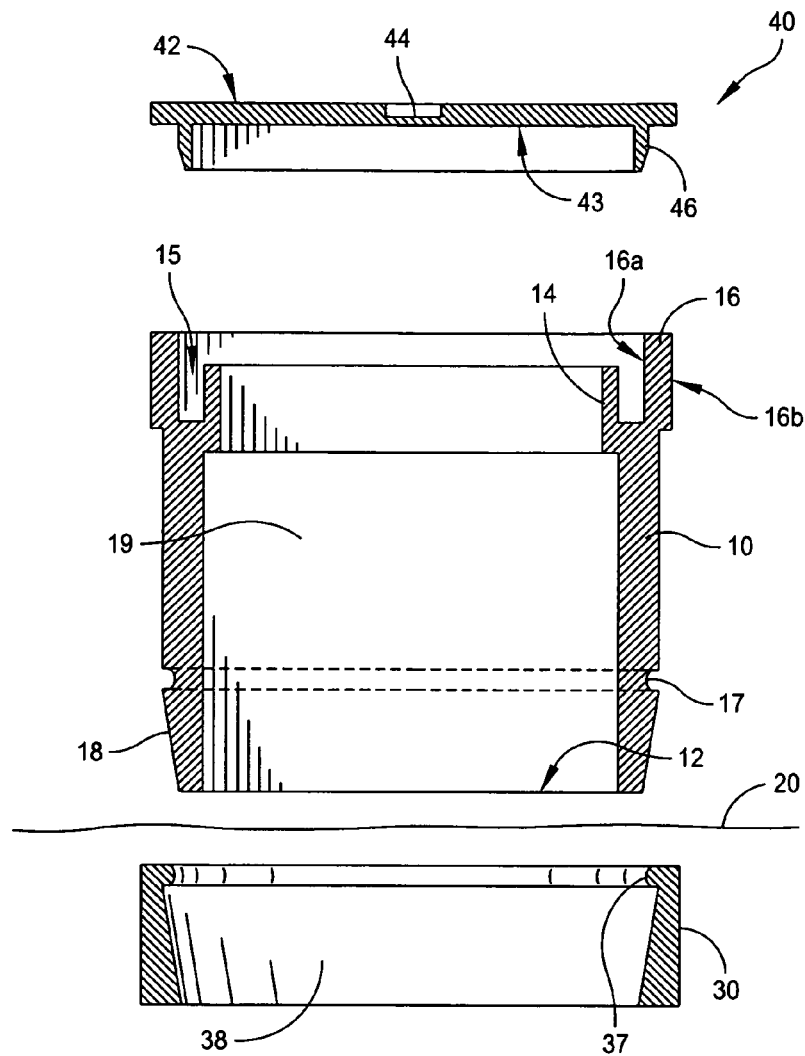
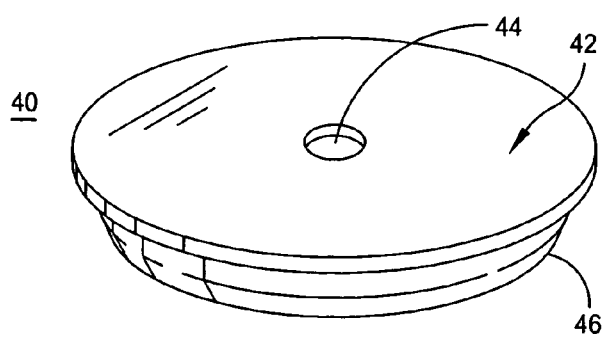
FIG. 5

SAMPLE CUP FOR USE IN X-RAY SPECTROSCOPY WITH INTERNAL OVERFLOW RESERVOIR

FIELD OF THE INVENTION

The present invention relates to an x-ray spectroscopy sample container cup having an internal reservoir for accommodating sample overflows.

BACKGROUND OF THE INVENTION

Spectroscopy is a science where a sample substance is analyzed by means of the spectra of light the sample absorbs or emits. Technological advancements in both wavelength-dispersive (WD-XRF) and energy-dispersive (ED-XRF) X-ray fluorescence instrumentation enable the spectroscopic analysis of virtually all types of sample materials. In this technology, sample cups or sample receptacles are employed to hold or contain liquid, solid and powdered specimens. Many conventional prior art sample cups consist of four components. The four components include a cell body with at least one open end; a thin film of material capable of covering the open end of the cell body; an annular collar used to pull the thin film of material taut over the open end of the cell body; and a snap-on retainer ring used to secure the thin film of material in place. The thin film of material encloses a sample substance within the cell body and provides a sample surface plane which is exposed to an excitation source, such as an X-ray tube, during the analysis. Such conventional prior art cups are exemplified by U.S. Pat. No. Des. 238,693 entitled "CELL FOR X-RAY SPECTROSCOPY OR SIMILAR ARTICLE" issued on Feb. 3, 1976 to Monte J. Solazzi; U.S. Pat. No. 4,409,854 entitled "SAMPLE CUP WITH VENTING MEANS FOR USE IN X-RAY SPECTROSCOPY" issued on Oct. 18, 1983 to Michael C. Solazzi; U.S. Pat. No. 4,643,033 entitled "SAMPLE CUP FOR USE IN X-RAY SPECTROSCOPY" issued on Feb. 17, 1987 to Monte J. Solazzi; U.S. Pat. No. 4,665,759 entitled "SAMPLE CUP WITH A CANTILEVER BEAM VENTING MEANS" issued on May 19, 1987 to Monte J. Solazzi; U.S. Pat. No. 4,698,210 entitled "SAMPLE CUP APPARATUS FOR USE IN X-RAY SPECTROSCOPY EMPLOYING SELECTIVELY OPERATED VENTING MEANS" issued on Oct. 6, 1987 to Michael C. Solazzi; U.S. Pat. No. 5,451,375 entitled "APPARATUS FOR TRIMLESS SAMPLE CUP USED IN X-RAY SPECTROSCOPY" issued on Sep. 19, 1995 to Monte J. Solazzi; U.S. Pat. No. 5,454,020 entitled "SAMPLE CUP ADAPTED FOR UPRIGHT HORIZONTAL AND INCLINED SAMPLE PLANE GEOMETRY SYSTEMS" issued on Sep. 26, 1995 to Monte J. Solazzi; and U.S. Pat. No. 5,630,989 entitled "APPARATUS FOR TRIMLESS SAMPLE CUP USED IN X-RAY SPECTROSCOPY" issued on May 20, 1997 to Monte J. Solazzi.

In order to equalize pressure and eliminate distension of the sample surface plane, some sample cups are provided with a venting means. The venting means may be activated to provide pressure equalization between the inside and outside of the cup. Other sample cup designs include a main cell component with both ends opened. This double open-ended cup allows for attachment of the thin film sheet prior to the introduction of the sample. This design is useful for applications in an environment where continuous venting is desired from the moment of sample introduction.

In some situations, the spectroscopic analysis may be conducted in a vacuum or pressurized inert gas environment. In order to equalize the pressure between the inside and outside of the sample cups, some of these prior art sample cups have a vent hole. In addition, those prior art sample cups with the vent hole have the reservoir space on the exterior surface of the sample cups for catching any specimen material that may overflow out of the vent holes. However, because these reservoir spaces are provided on a cap or a cap-like structure that encloses the sample cup, if the sample cup is to be left open during the spectrochemical analysis with out the cap, the reservoir is no longer available.

Thus, there is a need for an improved sample cup that may be placed in the spectrochemical analysis chamber with its top end open and still having a reservoir space to accommodate overflowing sample material during the spectrochemical analysis.

SUMMARY OF THE INVENTION

According to an aspect of the present invention, a sample cup for retaining a specimen to be subjected to spectrochemical analysis is disclosed. The sample cup comprises a cell body of a cylindrical configuration having an open top end and an open bottom end and defining a hollow between the two open ends. The open top end has an outer wall and an inner wall encircling the open top end. The outer wall and the inner wall extend axially and are positioned in concentric relationship with one another and form a reservoir space between them. The sample cup further comprises a means for covering the opened bottom end of the cell body when a specimen is contained within the hollow.

When conducting a spectrochemical analysis on a sample that heats up from excitation by the X-ray and therefore expands during the analysis, the reservoir space formed between the concentric inner and outer walls will hold the overflowing sample material and prevent it from spilling over into the spectrochemical analysis sample chamber. Inadvertent spillage into the x-ray analytical system is thereby avoided together with the time-consuming decontamination clean-ups.

Alternatively, rather than accommodating overflowing sample material, the inner wall of the cell body may be used to ensure that a predetermined quantity of sample is dispensed into the sample cup. The height of the inner wall of the cell body may be set equal to the height of the sample material equating to a predetermined quantity of the sample. Any excess sample material dispensed into the sample cup will overflow into the reservoir space.

In a preferred embodiment, the inner wall of the open top end is shorter than the outer wall of the open top end such that the expanding specimen material can flow over the inner wall into the reservoir space and the taller outer wall prevents the specimen from spilling out of the sample cup.

The means covering the open bottom end of the cell may comprise a thin sheet of polymer stretched over the open bottom end and a snap-on retaining ring positioned about an outer edge of the cell body near the open bottom end to hold the thin sheet of polymer in place.

The cell body has a peripheral groove around an outer surface thereof and located nearer the open bottom end to cooperate with and retain the snap-on retaining ring. The snap-on retaining ring has an inwardly extending peripheral ridge about its top opening and adapted to cooperate with the peripheral groove in the cell body achieving a snap-fit arrangement to securely hold the thin sheet of polymer between the cell body and the snap-on retaining ring.

The sample cup according to another embodiment of the present invention may include a friction-fitting cap member for sealing the open top end of the cell body after the specimen is placed inside the sample cup. The cap member may have a circular disk-like shape having a top surface and a bottom surface. One or more peripherally disposed sidewall extends downwardly from the bottom surface of the cap. The side wall frictionally engages the inner surface of the outer wall for sealing the top end opening of the cell body.

BRIEF DESCRIPTION OF THE DRAWINGS

FIG. 4 is a cross-sectional view of the sample cup assembly of FIG. 3 including an optional cap.

FIG. 5 is a perspective view of the cap shown in FIG. 4.

The features shown in the above referenced drawings are not intended to be drawn to scale nor are they intended to be shown in precise positional relationship. Like reference numbers indicate like elements.

DETAILED DESCRIPTION OF THE INVENTION

Figure 1:
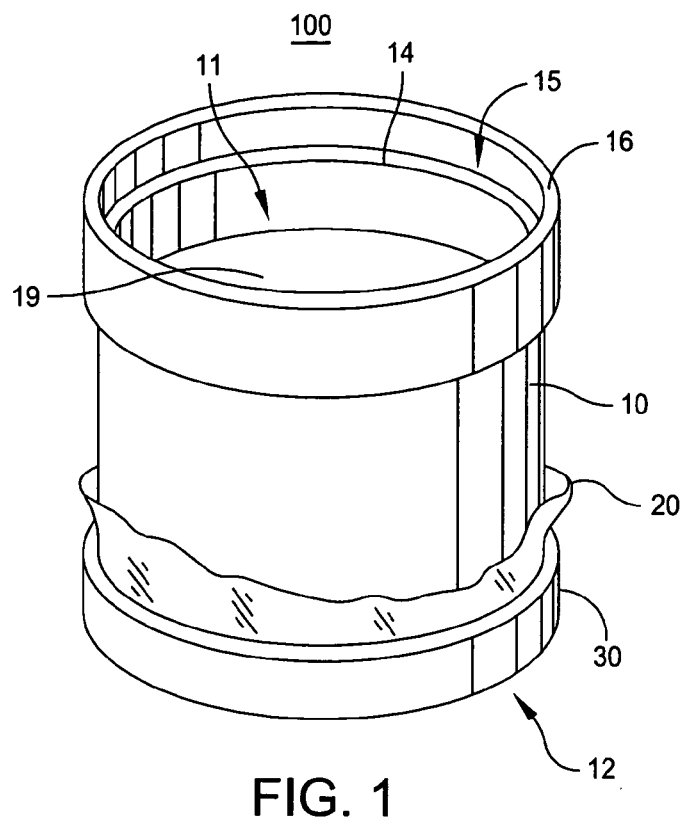
FIG. 1 is a perspective view of a sample cup according to an embodiment of the present invention.
Figure 2:
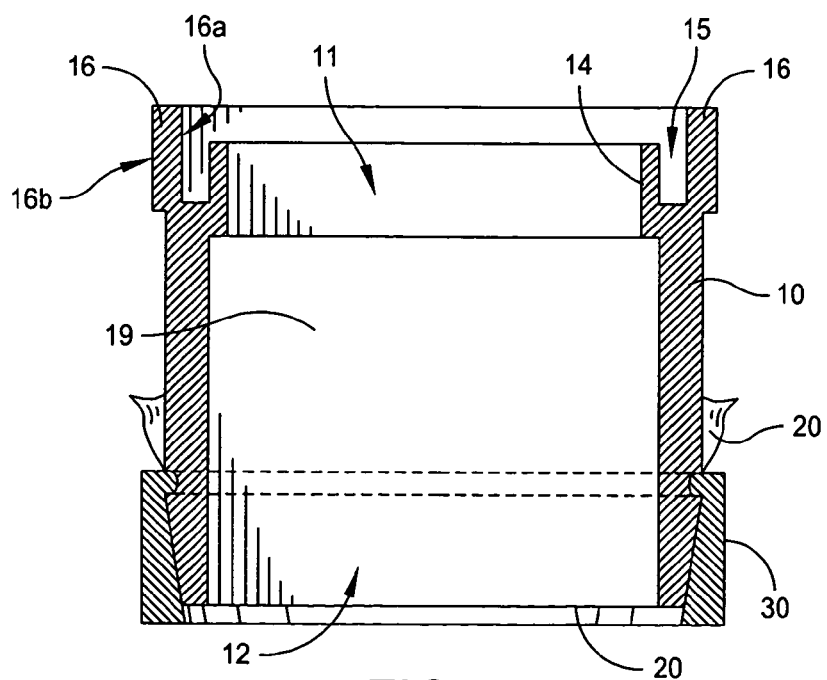
FIG. 2 is a cross-sectional view of the sample cup of FIG. 1.

Referring to FIGS. 1 and 2, there is shown a perspective view of assembled sample cup 100 for x-ray spectroscopy according to an embodiment of the present invention. The sample cup 100 comprises a cell body 10 of a cylindrical configuration. The cell body 10 has an open top end 11 and a bottom end 12. The bottom end 12 of the cell body 10 is an open structure but when assembled into a sample cup 100 as illustrated in FIGS. 1 and 2, the bottom end 12 is closed by a thin film sheet 20 of polymeric material secured and held in place around the bottom end 12 by a snap-on retaining ring 30. The cell body 10 and the thin film sheet 20 define a hollow 19 inside the sample cup 100 for holding a spectroscopy sample material (not shown). The top end 11 of the cell body 10 is configured to have an inner wall 14 and an outer wall 16 encircling the open top end 11. The inner wall 11 and the outer wall 16 extend axially and are positioned concentrically with respect to one another with a spacing therebetween, thus forming a reservoir space 15 between them. The outer wall 16 has an inner surface 16a and an outer surface 16b. The assembled sample cup 100 has a hollow space 19 defined by the cell body 10 and the thin film sheet 20 for holding the spectroscopy sample material (not shown).

Because the sample cup 100 is open at the top end 11, the spectroscopy sample may be introduced into the hollow space 19 through the top end opening after the bottom end 12 is closed by the thin film sheet 20.

Figure 3:
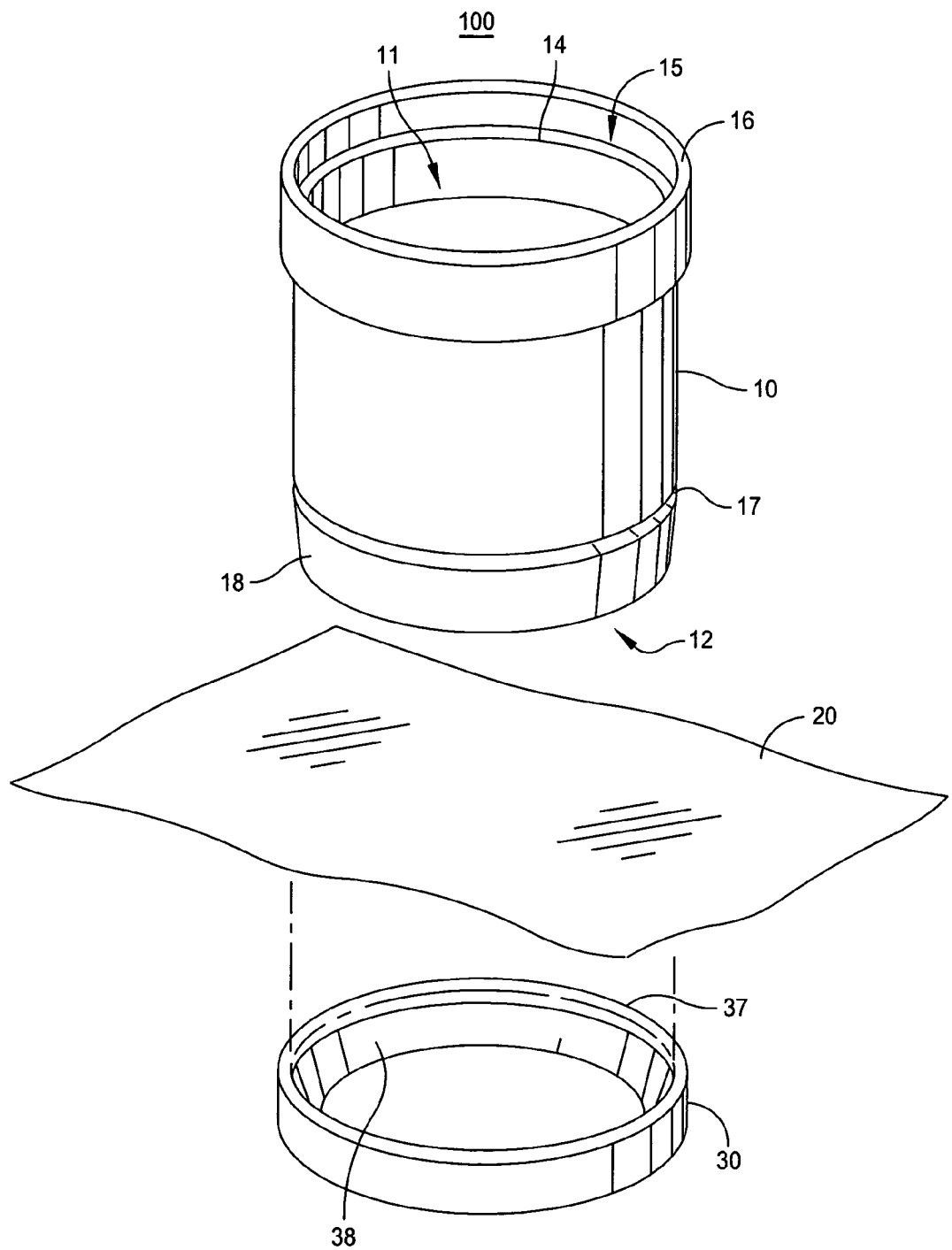
FIG. 3 is an assembly view of the sample cup of FIG. 1.

Referring to FIGS. 3 and 4, a perspective assembly view and a cross-sectional assembly view of the sample cup 100 are shown, respectively. The cell body 10 is a cylindrical structure having an open top end 11 and an open bottom end 12. The cell body 10 near its top end 11 is configured to have concentrically positioned inner wall 14 and an outer wall 16. Formed and defined by the inner wall 14 and the outer wall 16 is a reservoir space 15. On the exterior surface of the cell body 10 near the bottom end 12 is a peripheral groove 17 around the outer surface of the cell body 10 for accommodating the snap-on retaining ring 30. A bottom collar portion 18 between the peripheral groove 17 and the bottom end 12 of the cell body 10 is tapered to allow for easy insertion of the snap-on retaining ring 30.

The snap-on retaining ring 30 has an inwardly extending peripheral ridge 37 about a top opening and adapted to cooperate with the peripheral groove 17 on the cell body 10. When the snap-on retaining ring 30 is placed over the bottom end 12 of the cell body and slid over the bottom collar portion 18, the peripheral ridge 37 snaps into the peripheral groove 17. The inner surface 38 of the snap-on retaining ring 30 is tapered to match the taper of the bottom collar portion 18 of the cell body 10.

To close or seal the bottom end 12 of the cell body 10, a thin film sheet 20 is placed over the open bottom end 12 and held in place by sliding the snap-on retaining ring 30 over the bottom collar portion 18 until the ridge 37 of the snap-on retaining ring 30 snapingly engages the peripheral groove 17. The snapping engagement between the internal ridge 37 of the snap-on retaining ring 30 and the peripheral groove 17 of the cell body grips the thin film sheet 20 in sufficient manner to maintain a flat sample plane necessary for the spectrochemical analysis.

The thin film sheet 20 may be a polymer sheet, such as Mylar®, that is transparent to the radiant energy used in the spectrochemical analysis. The possible compositions of such thin film materials are well known in the art and need not be set forth herein at length, but polyethylene is an example.

In an another embodiment of the present invention, the sample cup 10 may also include a cap 40 as illustrated in FIGS. 4 and 5. The cap 40 is a substantially a disc-like structure having a top surface 42 and a bottom surface 43. Extending downwardly from the bottom surface 43 is a sidewall 46. As illustrated, the sidewall 46 is peripherally located on the bottom surface 43 of the cap 40. The sidewall 46 is configured and dimensioned to frictionally fit against the inner surface 16a of the outer wall 16 of the cell body 10. For example, to achieve the frictional fit, the sidewall 46 may have a tapered outer surface whose diameter near the base of the sidewall 46 (i.e., near the bottom surface 43 of the cap 40 is at its greatest and is slightly larger than the diameter of the inner surface 16a of the outer wall 16 of the cell body 10. Thus, when the cap 40 is pressed into the top end 11 of the cell body 10, the tapered outer surface of the sidewall 46 frictionally engages the inner surface 16a and securely holds the cap 40 in place. The cap 40 may also be provided with an optional vent 44. The vent 44 is a portion of the cap 40 that is intentionally made thin so that the thin portion can be punctured using a sharp object creating a vent hole. This feature is useful when an equalization of the pressures between the inside and the outside of the sample cup 100. Alternatively, a thin polymer film sheet may be used to close the top end.

Figure 8:
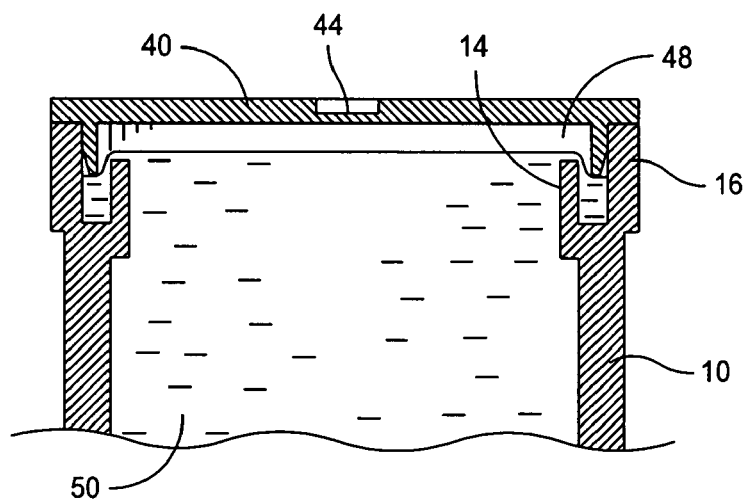
FIG. 8 is a partial view of a cross-sectional view of the sample cup according to another embodiment of the present invention.

By adjusting the height of the inner wall 14, the sample cup 100 may be customized to adjust the amount of volume expansion of a sample material that is required before the sample material overflows from the internal hollow 19 of the sample cup 100 into the reservoir space 15. As illustrated in FIG. 8, in a preferred embodiment of the present invention, the inner wall 14 may be sufficiently shorter than the outer wall 16 in order to maintain some space 48 between the cap 40 and the inner wall 14 when a cap is used. But the specific dimensions of the inner wall 14, the outer wall 16 and spacing 13 between the two walls may be configured and adjusted according to the particular size of the reservoir space 15 that is desired for a given application.

Figure 6:
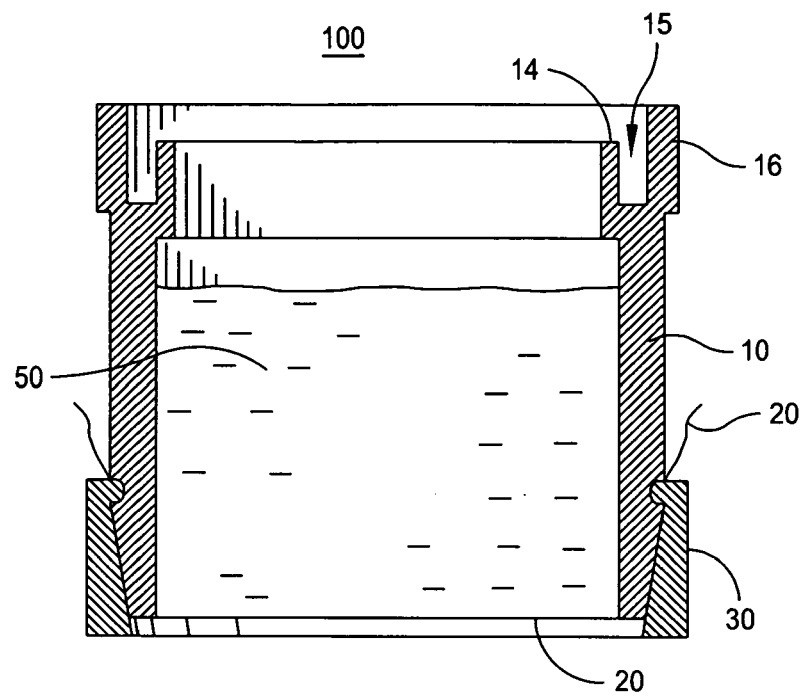
FIG. 6 is a cross-sectional view of the sample cup of FIG. 1 with a sample material inside the sample cup.
Figure 7:
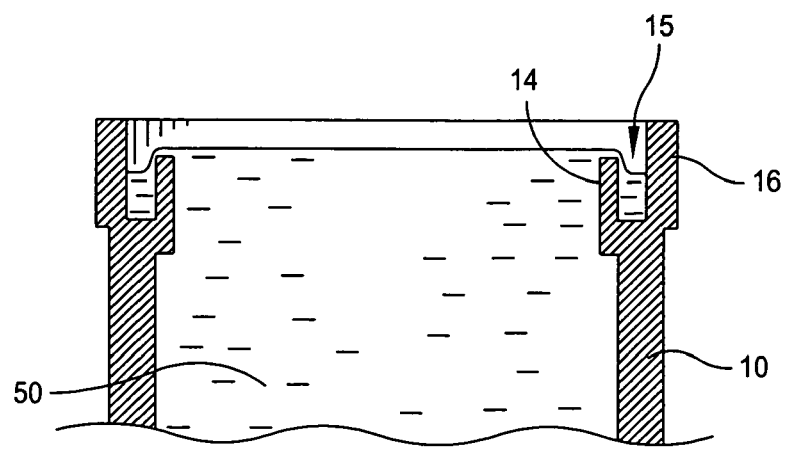
FIG. 7 is a partial view of the cross-sectional view of FIG. 6 in which the sample material is overflowing into the reservoir space of the sample cup.

Referring to FIGS. 6 and 7, the function of the reservoir space 15 according to the present invention is illustrated. In FIG. 6, a cross-sectional view of a sample cup 100 containing a liquid sample material 50 (e.g. oil) is shown. During an x-ray spectroscopy, the liquid sample material 50 is heated from excitation by the x-ray energy. As the liquid sample material 50 gets hotter, it expands in volume and the liquid sample material 50 will rise inside the sample cup 100. As illustrated in FIG. 7, if the volume expansion of the liquid sample material 50 is sufficiently large, the liquid sample material 50 will rise above the inner wall 14 and flow over. But the reservoir space 15 is sufficiently large to accommodate the over flowing liquid sample material 50 and prevent it from over flowing into the x-ray spectroscopy chamber.

All components of the sample cup 100 may be fabricated from an appropriate polymer such as polyethylene.

While the foregoing invention has been described with reference to the above embodiments, various modifications and changes can be made without departing from the spirit of the invention. Accordingly, all such modifications and changes are considered to be within the scope of the appended claims.

What is claimed is:

1. A sample cup for retaining a specimen to be subjected to spectrochemical analysis, comprising:

a cell body of a cylindrical configuration having an open top end and an open bottom end and defining a hollow between the two open ends, the open top end having an outer wall and an inner wall encircling the open top end, the outer wall and the inner wall extending axially and positioned in concentric relationship with one another, said outer wall and said inner wall forming an internal reservoir space therebetween, said inner wall being positioned sufficiently below a top edge of said outer wall to allow a sample material to flow over the inner wall into the internal reservoir space, and the outer wall prevents overflow of the sample material from the internal reservoir space; and a cap for sealing the open top end of the cell body, the cap having a top surface and a bottom surface and a peripherally disposed sidewall extending downwardly from the bottom surface of the cap, wherein the sidewall frictionally and continuously engages solely the inner surface of the outer wall of the top end of the cell body.

2. The sample cup of claim 1, further comprising a means covering the opened bottom end of the cell body when a specimen is contained within the hollow.

3. The sample cup of claim 1, wherein the inner wall of the open top end is shorter than the outer wall of the open top end.

4. The sample cup of claim 2, wherein the means covering the open bottom end of the cell body comprises a tin sheet of polymer stretched over the open bottom end; and a snap-on retaining ring positioned about an outer edge of the cell body near the open bottom end to hold the thin sheet of polymer in place.

5. The sample cup of claim 4, wherein the cell body has a peripheral groove around an outer surface thereof and located near the open bottom end to cooperate with and retain the snap-on retaining ring.

6. The sample cup of claim 5, wherein the snap-on retaining ring has an inwardly extending peripheral ridge about a top opening and adapted to cooperate with the peripheral groove on the cell body.

7. The sample cup of claim 4, wherein the cell body and the snap-on retaining ring are fabricated from a polymer material.

8. A sample cup for retaining a specimen to be subjected to spectrochemical analysis, comprising:

a cell body of a cylindrical configuration having an open top end and an open bottom end and defining a hollow between the two open ends;

the open top end having an outer wall and an inner wall encircling the open top end, the outer wall and the inner wall extending axially and positioned in concentric relationship with one another and forming an internal reservoir space therebetween, the outer wall having an outer surface and an inner surface; and a cap for sealing the open top end of the cell body, the cap having a top surface and a bottom surface and a peripherally disposed sidewall extending downwardly from the bottom surface of the cap, wherein the sidewall frictionally and continuously engages solely the inner surface of the outer wall of the top end of the cell body, wherein said inner wall is positioned below a to edge of said outer wall to allow a sample material to flow over the inner wall into the internal reservoir space, and the outer wall prevents overflow of the sample material from the internal reservoir space.

9. The sample cup of claim 8, further comprising a means covering the opened bottom end of the cell body when a specimen is contained within the hollow.

10. The sample cup of claim 8, wherein the inner wall of the open top end is shorter than the outer wall of the open top end.

11. The sample cup of claim 8, wherein the means covering the open bottom end of the cell body comprises a thin sheet of polymer stretched over the open bottom end; and a snap-on retaining ring positioned about an outer edge of the cell body near the open bottom end to hold the thin sheet of polymer in place.

12. The sample cup of claim 11, wherein the cell body has a peripheral groove around an outer surface thereof and located near the open bottom end to cooperate with and retain the snap-on retaining ring.

13. The sample cup of claim 12, wherein the snap-on retaining ring has an inwardly extending peripheral ridge about a top opening and adapted to cooperate with the peripheral groove on the cell body.

14. The sample cup of claim 11, wherein the cell body, the snap-on retaining ring and the cap are fabricated from a polymer material.

15. The sample cup of claim 14, wherein the polymer material is polyethylene.

16. The sample cup of claim 7, wherein the polymer material is polyethylene.

* * * * *

UNITED STATES PATENT AND TRADEMARK OFFICE
CERTIFICATE OF CORRECTION

PATENT NO. : 7,722,821 B2 Page 1 of 1
APPLICATION NO. : 10/990994
DATED : May 25, 2010
INVENTOR(S) : Monte J. Solazzi It is certified that error appears in the above-identified patent and that said Letters Patent is hereby corrected as shown below:

On the Title page item (73), "Chemplax" should be deleted and replaced with --Chemplex--, and
Title page item (74), "Keens" should be deleted and replaced with --Keene--.

In Claim 4, line 2, the word "tin" should be deleted and replaced with --thin--.

Signed and Sealed this

Tenth Day of August, 2010

David J. Kappos
*Director of the United States Patent and Trademark Office*